United States Patent [19]

Jacobs

[11] 4,413,986
[45] Nov. 8, 1983

[54] TAMPON ASSEMBLY WITH MEANS FOR STERILE INSERTION

[76] Inventor: Henry R. Jacobs, 525 Grove St., Evanston, Ill. 60201

[21] Appl. No.: 205,678

[22] Filed: Nov. 10, 1980

[51] Int. Cl.$^3$ ............................................. A61F 15/00
[52] U.S. Cl. ......................................................... 604/14
[58] Field of Search ....................... 128/263, 270, 285; 604/11–18

[56] References Cited

U.S. PATENT DOCUMENTS

| | | | |
|---|---|---|---|
| 2,413,480 | 12/1946 | Winter | 128/263 |
| 2,922,423 | 1/1960 | Rickard et al. | 128/263 |
| 3,499,447 | 3/1970 | Mattes et al. | 128/263 |
| 4,286,594 | 1/1981 | Cunningham | 128/263 |
| 4,318,404 | 3/1982 | Cunningham | 128/263 |

FOREIGN PATENT DOCUMENTS 7217313 6/1974 Netherlands ........................ 128/263

*Primary Examiner*—C. Fred Rosenbaum
*Attorney, Agent, or Firm*—Fitch, Even, Tabin & Flannery

[57] ABSTRACT

A tampon assembly includes a tampon and a withdrawal cord, an insertion tube containing the tampon, a guide tube telescoped around the insertion tube, a flexible sheath attached to the inner end of the guide tube and tucked into the inner end of the insertion tube, and a pusher to eject the tampon from the insertion tube. When the user inserts the tampon by placing the guide tube against her introitus, plunging the insertion tube inward so that a portion thereof penetrates the vagina and plunging the pusher inward to eject the tampon from the insertion tube, the flexible sheath sheathes the penetrating portion of the insertion tube thereby maintaining the sterility of the insertion.

8 Claims, 9 Drawing Figures

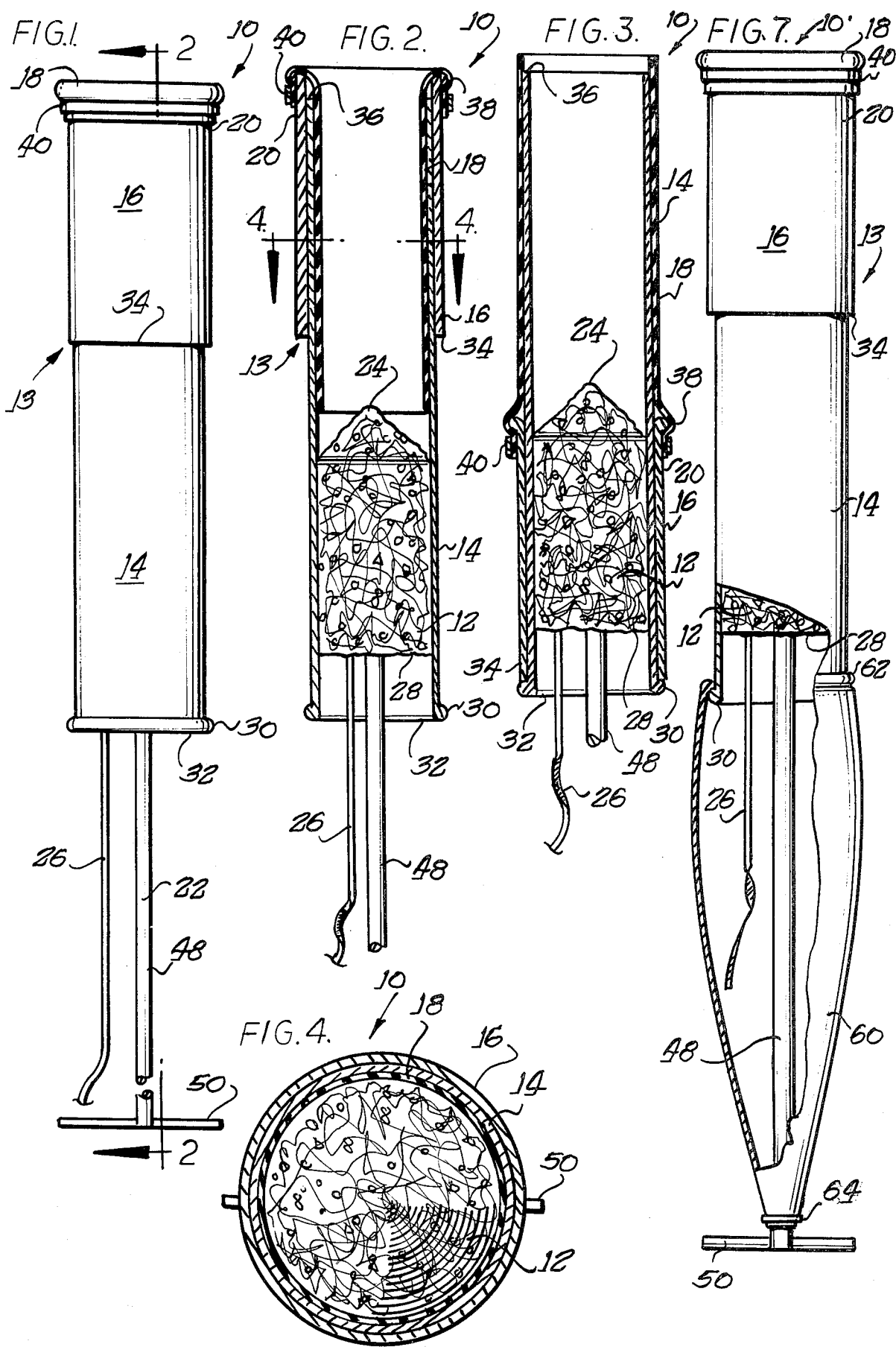

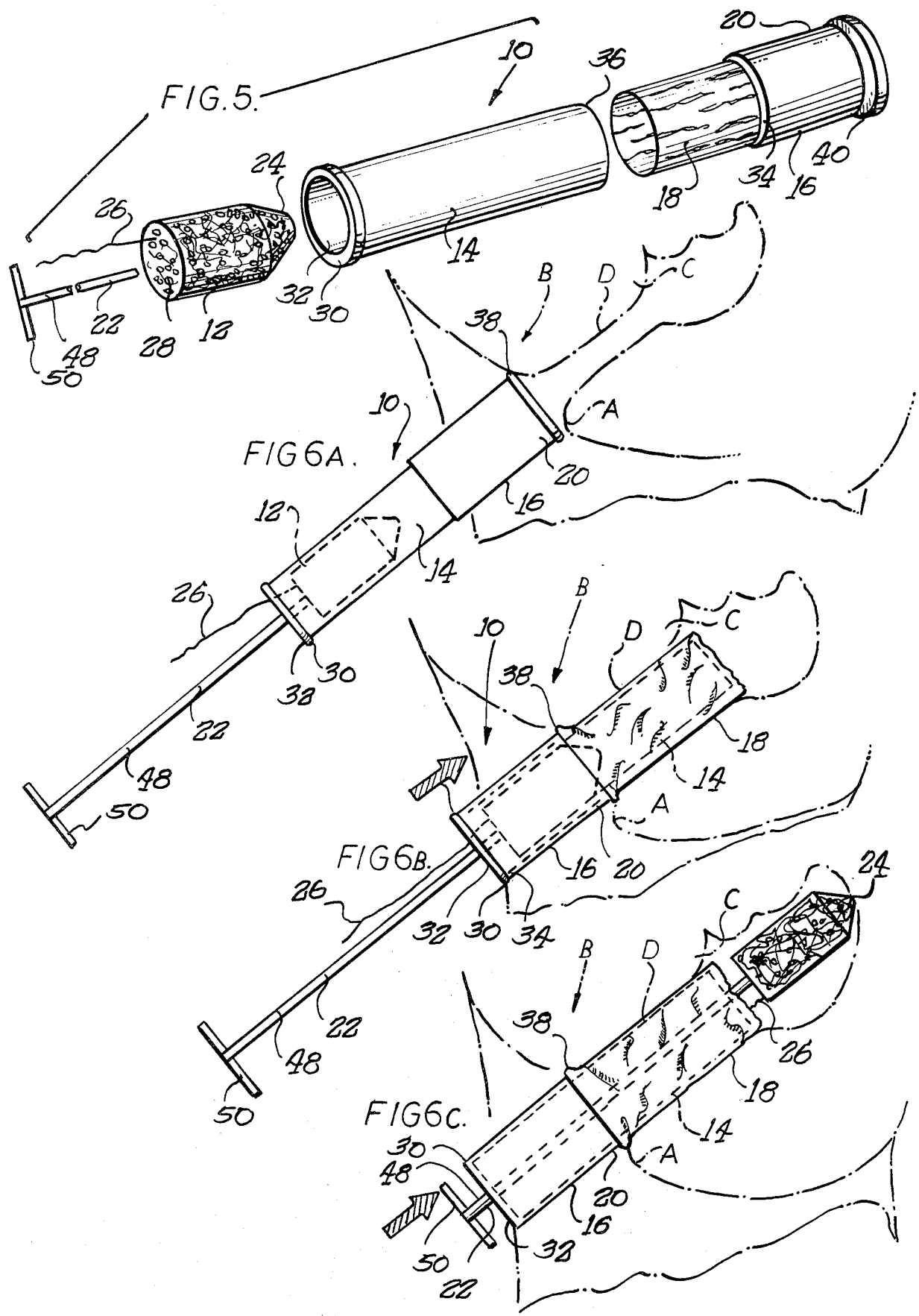

TAMPON ASSEMBLY WITH MEANS FOR STERILE INSERTION

The present invention relates to vaginal tampons and more particularly to tampons which may be inserted in a sterile manner.

BACKGROUND OF THE INVENTION

A newly recognized illness of women called toxic shock syndrome has recently been reported. (FDA Bulletin July 1980). Toxic shock syndrome generally occurs during the menstrual period and appears to be associated with the use of tampons which carry bacteria into the inner regions of the vagina close to the uterus where the menstrual fluid provides a good growth medium for bacteria. Staphylococcus aureous is almost always found to be present in toxic shock syndrome. The mortality rate of women who experience toxic shock syndrome is between three and ten percent.

Tampons which are commonly about one and one-half inches long are inserted into the vagina beyond the constricting muscles, generally about two inches. A tampon may be inserted into the vagina with a pusher, such as a stick removably attached to the outer or trailing end of the tampon, or may be encased in a plastic applicator which is inserted into the vagina and from which the tampon is pushed and ejected. In either case, a portion of the tampon or applicator which is inserted into the vagina will likely be touched by the user's hand and/or will be exposed to the external vagina during insertion and contaminated thereby, whereby bacteria and viruses, capable of causing toxic shock or other uterine or vaginal infections, are carried deep into the vagina.

SUMMARY OF THE INVENTION

A tampon assembly for sterile insertion of a tampon into the vagina has a semirigid insertion tube, containing the tampon, telescoped inside a semirigid guide tube having a flexible sheath secured to its inner end which is tucked back into the insertion tube. The user aligns the assembly with the vaginal canal and plunges the insertion tube inward of the guide tube so that a portion of the insertion tube enters the vagina while the flexible sheath extends to sheathe the portion of the insertion tube within the vagina. Thereafter, a pusher is used to eject the tampon from the insertion tube to locate the tampon in the vagina beyond the constricting muscles.

BRIEF DESCRIPTION OF THE DRAWINGS

FIG. 1 is an elevation view of a tampon assembly embodying various features of the present invention, the assembly shown in its pre-insertion position.

FIG. 2 is a cross-sectional view taken along line 2—2 of FIG. 1.

FIG. 3 is a cross-sectional view similar to FIG. 2 showing the tampon assembly in its insertion position.

FIG. 4 is a cross-sectional view of the assembly taken along line 4—4 of FIG. 2.

FIG. 5 is an exploded perspective view of the tampon assembly.

FIGS. 6a-c illustrate the insertion of the tampon into the vagina, FIG. 6a showing the assembly being placed against the introitus, FIG. 6b showing the inside insertion tube plunged fully into the outside guide tube, and FIG. 6c showing the tampon ejected from the inside tube into the vagina beyond the constricting muscles thereof.

FIG. 7 is an elevation view, partially cut away, of an alternative embodiment of the present invention in which an enclosed wrap maintains the sterility of the outer end of the assembly.

DETAILED DESCRIPTION OF THE PREFERRED EMBODIMENTS

In accordance with the present invention, a tampon assembly 10 has a tampon 12 (FIG. 2) and a container 13 including a semirigid inside insertion tube 14 which carries the tampon and which is telescoped in a semirigid outside guide tube 16 having a sterile flexible sheath 18 secured to an end 20 thereof and tucked into the insertion tube so that when the assembly is placed against the introitus A (FIG. 3) of the vagina B and the insertion tube is plunged inward of the guide tube and into the vagina, the flexible sheath extends to sheathe that portion of the insertion tube in the vagina, thereby providing sterile insertion of the tampon. An ejector means or pusher 22 is used to eject the tampon 12 from the insertion tube 14 into the vagina beyond the constricting muscles C.

So that the invention may be more fully understood, the tampon assembly 10 will now be described in greater detail. To facilitate discussion, the ends of the assembly 10 and members thereof which are directed toward the body will be described as the inner ends.

The vaginal tampon 12 is of conventional design, being formed of compressed fibrous material and having a pointed inner end 24 to ease its insertion and having a withdrawal cord 26 secured to its outer end 28 which extends from the inserted tampon outward of the introitus A where it may be pulled to remove the used tampon from the vagina B. The tampon 12 itself does not constitute a part of this invention, and variations of tampon design known to those skilled in the art may be made without departing from the scope of the present invention.

The insertion tube 14 is cylindrical and is sufficiently narrow, e.g., about one-half inch in diameter, that it may be inserted into the vaginal canal D. The compressed tampon 12 bulges against the wall of the insertion tube 14 and is thereby held in position. The insertion tube 14 is preferably semirigid, having sufficient rigidity to part the walls of the vaginal canal D as it is plunged therethrough, but sufficiently flexible to deform and prevent injury should it be inserted incorrectly and pushed against sensitive tissue. A flange 30 around the outer end 32 of the insertion tube 14 serves as a stop which abuts the outer end 34 of the guide tube 16 when the insertion tube 14 is plunged inward as shown in FIGS. 3 and 6b.

The guide tube 16 is similarly cylindrical with an inside diameter substantially equal to the outside diameter of the insertion tube 14 and is movably telescoped therearound. Preferably, the guide tube 16 fits tightly around the insertion tube 14 and frictionally maintains the tubes in telescoping relationship to each other without slipping apart prior to use. The guide tube 16, like the insertion tube 14, is preferably semirigid and generally is formed of the same material; however, the guide tube may be thicker and less flexible as it is not intended that it be inserted into the body. Preferably, both semirigid tubes 14, 16 will be formed of a polymer which will degrade in water so that the tubes may be flushed down the toilet.

The guide tube 16 is shorter than the insertion tube 14, so that when plunged into the vagina B, the insertion tube is displaced between about 1½ to 2 inches as it is moved from its pre-insertion position (FIG. 1) with its inner end 36 generally flush with the inner end 20 of the guide tube 16 to its insertion position (FIG. 2) with its outer end 32 generally adjacent the outer end 34 of the guide tube.

A flange 38 (FIGS. 2, 3), disposed around the inner end 20 of the guide tube 16 for placement against the introitus A, helps to prevent the guide tube from penetrating the vagina B. The outside diameter of the flange 38 is preferably at least ⅜ inch in diameter.

The flexible sheath 18 is preferably formed of thin elastomeric material, such as silicone rubber, and has a diameter slightly greater than the outside diameter of the insertion tube 14 to form a loose sheath therearound in the inserted position. A thickened elastomeric band 40 at the inner end of the flexible sheath 18 is pulled over the flange 38 at the inner end 20 of the guide tube 16 where it binds around the guide tube and is prevented by the flange from slipping off during tampon insertion. The flexible sheath 18 is folded from its outer end, around the inner ends 20, 36 of the semirigid tubes 14, 16 and into the insertion tube inward of the tampon 12. The flexible sheath 18 is generally equal in length to the difference in length of the insertion and guide tubes so that the portion of the insertion tube 14 which is plunged into the vagina B is at all times fully sheathed by the flexible sheath 18. The exterior surface of the flexible sheath 18 may be lubricated to facilitate its insertion.

The pusher 22 has an applicator stick 48 having an inner end which impales the outer end of the tampon 12 to removably attach the stick thereto. The outer end may be attached to an optional crosspiece 50. The stick 48 is somewhat longer than the insertion tube 14, so that when the user plunges the pusher 22 completely inward, the tampon 12 is ejected from the inner end 36 of the insertion tube. The crosspiece 50 is longer than the inside diameter of the insertion tube 14 and stops inward movement of the pusher 22 when it abuts the outer end 32 of the insertion tube, thereby preventing the pusher from accidentally being inserted in the vagina.

The tampon assembly 10 is assembled under sterile conditions and packaged in a sterile wrapper (not shown) with the assembly in its pre-insertion position. The wrapper preferably is designed to be opened so that the user will grasp the outer end first and not contaminate the inner end to which the flexible sheath 18 is attached.

Grasping the assembly 10 with her left thumb and two fingers, the use will align the assembly with her vaginal passageway as may be described in accompanying directions, and shown in FIG. 6a. She places the assembly 10 with the flange 38 against her introitus A and plunges the insertion tube 14 through the guide tube 16 and into the vagina B as far as it will go with fingers of her right hand as shown in FIG. 6b. As the insertion tube 14 is plunged inward, the flexible sheath 18 is pulled over the inner end 32 of the insertion tube and extends along the exterior thereof. The loosely fitting flexible sheath 18 is held along the exterior of the insertion tube 14 by the conforming walls of the vaginal passageway. When the insertion tube 14 is plunged fully into the guide tube 16, the flexible sheath 18 is substantially fully extended and removed from the insertion tube and permits passage of the tampon 12 through its open inner end. Thereafter, the user plunges the pusher 22 fully inward (FIG. 6c) until the crosspiece 50 abuts the outer end 30 of the insertion tube 16.

The ejected tampon 12 is fully beyond the constricting muscles C of the vaginal canal D and the user removes the assembly applicator members by pulling the exposed guide tube 16 outward. The abutment of the outer end 34 of the guide tube 16 against the flange 30 of the insertion tube 14 and the abutment of the outer end 32 of the insertion tube against the crosspiece 50 of the pusher 22 causes the insertion tube and the pusher to follow the guide tube as it is pulled away from the introitus A. A slight pull on the loosely held pusher 22 dislocates it from the outer end 28 of the tampon 12. The flexible sheath 18 is also pulled along with the guide tube 16. The withdrawal of the applicator apparatus helps to pull the end of the withdrawal cord 26 outward so that it protrudes from the introitus A. With a slight tug on the withdrawal cord 26 the user may position the tampon 12 in the inner end of her constricting muscles C.

Illustrated in FIG. 7 is an alternative embodiment of the tampon assembly 10', in which a flexible enclosure 60 protects the outer end of the assembly from contamination. The enclosure 60 is secured at one end around the outer end 32 of the insertion tube 14 and at the other end around the pusher 22 to maintain the sterility of the outer end of the tampon 12 and that portion of the pusher 22 which enters the vagina B. The enclosure 60 shown in FIG. 7 has an elastomeric end band 62 around the insertion tube 14 and an elastomeric end band 64 around the pusher 22. As the pusher 22 is plunged inward, the enclosure 60 folds up. Alternatively, a suitable enclosure for the outer end of the assembly 10 may be formed of paper and attached by an adhesive to the pusher 22 and insertion tube 14.

While the invention has been described in terms of specific preferred embodiments, modifications obvious to one with ordinary skill in the art may be made without departing from the scope of the invention. For example, instead of a stick type pusher, the pusher may be a third semirigid tube which telescopes inside of the insertion tube. Grooved rings around the guide tube may be provided to facilitate grasping thereof. Because tampons may be shelved for several years before use, an elastomeric band maintained in a stretched position over a long time may lose resiliency. Accordingly, to insure that the flexible sheath will not slip off during insertion, it may be desirable to permanently affix the sheath to the guide tube by gluing, welding, etc.

The telescoping arrangement of two tubes, in the desribed preferred embodiments, provides guidance for the tampon through the vaginal canal. The sterility of tampon insertion may, however, be maintained in a simpler arrangement in which the tampon is contained in a single tube having a flexible sheath attached to its outer end and tucked back into the tube. The tube is placed against the introitus, and the tampon is ejected therefrom through he vaginal canal. As the tampon is ejected, it extends the sheath which provides a sterile passageway through the vaginal canal for the tampon.

The concept of the present invention in which an inside tube is plunged through a telescoping outside tube with a sterile flexible sleeve attached to its inner end may have other medical applications. Examples of alternative applications of the invention principle include catheterizations, including catheterizations of the cerebral ventricles, peritoneoscopy where instruments are inserted through the tubes, and abortions where the uterine cavity may be entered through the cervix in a sterile fashion to deposit an abortifacient.

Various features of the invention are set forth in the following claims.

What is claimed is:

1. A vaginal tampon assembly comprising:
   a tampon of absorbent material for insertion into the vagina and having withdrawal means,
   a semirigid first tube containing said tampon,
   ejector means to push said tampon from said first tube into the vagina,
   a semirigid second tube having an inside diameter substantially the same as the outside diameter of said first tube, said second tube disposed in telescoping relationship around said first tube, said second tube having means for preventing its insertion into the vagina when placed against the introitus of the vagina,
   a flexible sheath having an outer end secured to the inner end of said second tube and folded into the inner end of said first tube, whereby said tampon may be inserted into the vagina in a sterile manner by placing said inner end of said second tube against the introitus, plunging said first tube inward of said second tube to extend an inner portion thereof into the vagina while extending said flexible sheath therearound, and actuating said ejector means to push said tampon from the inner end of said first tube.

2. An assembly according to claim 1 wherein said insertion prevention means is a flange around the inner end of said second tube.

3. An assembly according to claim 2 wherein a thickened elastomeric band at the outer end of said flexible sheath is disposed around said second tube outward of and closely adjacent to said flange.

4. An assembly according to claim 1 wherein said first tube is longer than said second tube, and said first tube is plunged from a pre-insertion position with its inner end generally flush with the inner end of said second tube to an insertion position with its outer end closely adjacent to the outer end of said second tube.

5. An assembly according to claim 4 wherein said flexible sheath is generally equal in length to the difference in lengths of said first and second tubes whereby said inner portion of said first tube is fully sheathed by said flexible sheath while in the vagina.

6. A vaginal tampon assembly comprising:
   a tampon of absorbent material for insertion into the vagina and having withdrawal means,
   a semirigid first tube containing said tampon,
   ejector means to push said tampon from said first tube into the vagina,
   a semirigid second tube having an inside diameter substantially the same as the outside diameter of said first tube, said second tube disposed in telescoping relationship around said first tube,
   a flexible sheath having an outer end secured to the inner end of said second tube and folded into the inner end of said first tube, whereby said tampon may be inserted into the vagina in a sterile manner by placing said inner end of said second tube against the introitus, plunging said first tube inward of said second tube to extend an inner portion thereof into the vagina while extending said flexible sheath therearound, and actuating said ejector means to push said tampon from the inner end of said first tube, said first tube having a stop means at it outer end which abuts the outer end of said second tube to halt inward movement of said first tube.

7. An assembly according to claim 1 also including a wrap of flexible material with a first end secured around the outer end of said first tube and a second end secured around said ejector means sealing the outer end of said first tube and maintaining the sterility of a portion of said ejector means inward of said second end of said wrap.

8. A tampon assembly comprising:
   a tampon of absorbent material for insertion into the vagina,
   container means for said tampon, said container means having an open inner end and means at said open inner end for preventing insertion of said container means into the vagina when said inner end is placed against the introitus of the vagina,
   ejector means for pushing said tampon from said inner end of said container means, and
   a sterile flexible sheath having one end secured to said open inner end, said sheath having a length at least about equal to the distance through the vaginal canal from the introitus to the inner extent of the constricting muscles, said sheath folded into said open inner end of said container means and positioned in said container means inward of said tampon to be extended along the walls of the vaginal canal by the action of said ejector means pushing said tampon, forming a sterile passageway for said tampon through the vaginal canal.

* * * * *